United States Patent [19]

Feldstein et al.

[11] 4,044,798
[45] Aug. 30, 1977

[54] ADHESIVE BONDED HYDROTEST PLUG AND METHOD FOR USING THE SAME

[75] Inventors: Joel Gary Feldstein; Jeffrey Forsha Martin, both of Alliance, Ohio

[73] Assignee: The Babcock & Wilcox Company, New York, N.Y.

[21] Appl. No.: 641,102

[22] Filed: Dec. 15, 1975

[51] Int. Cl.² .............................................. F16L 55/10
[52] U.S. Cl. ........................................ 138/90; 138/89
[58] Field of Search ............................. 138/97, 90, 89; 73/49.1, 49.5; 156/294, 305

[56] References Cited

U.S. PATENT DOCUMENTS

| | | | |
|---|---|---|---|
| 1,841,974 | 1/1932 | Naylor | 138/90 |
| 2,062,527 | 12/1936 | Postlewaite | 73/49.5 |
| 2,155,602 | 4/1939 | Keulers | 138/90 |
| 2,241,526 | 5/1941 | Rosenkranz | 138/90 |
| 2,578,728 | 12/1951 | Musser | 73/49.5 |
| 2,808,852 | 10/1957 | Brant | 138/97 |
| 3,103,235 | 9/1963 | Stringham | 138/97 |
| 3,199,598 | 8/1965 | Loomis | 138/97 X |
| 3,213,674 | 10/1965 | Salcido et al. | 138/90 X |
| 3,606,913 | 9/1971 | Yie | 73/49.1 X |
| 3,762,446 | 10/1973 | Tungseth et al. | 138/97 |
| 3,834,422 | 9/1974 | Larson | 138/97 |
| 3,847,694 | 11/1974 | Stewing | 156/305 X |
| 3,919,880 | 11/1975 | Seyd et al. | 73/49.5 X |

FOREIGN PATENT DOCUMENTS

| | | | |
|---|---|---|---|
| 212,715 | 3/1924 | United Kingdom | 138/97 |
| 826,429 | 1/1960 | United Kingdom | 138/90 |

*Primary Examiner*—Richard E. Aegerter
*Assistant Examiner*—James E. Bryant, III
*Attorney, Agent, or Firm*—J. M. Maguire; V. M. Fazzari; A. Notaro

[57] ABSTRACT

The invention relates to a hydrotest plug useful in testing the structural integrity of pressure tube arrangements, piping and the like as well as a method for using the same. The hydrostatic test plug comprises a conventional plug with internal passages providing conduit means for injection of a fluid adhesive, air escape means and centering means.

2 Claims, 3 Drawing Figures

ADHESIVE BONDED HYDROTEST PLUG AND METHOD FOR USING THE SAME

BACKGROUND OF THE INVENTION

Developments in a number of areas of technology have shown a trend favoring the use of high pressure installations. Steam generators, power boilers and chemical reactors are only a few of the areas where high pressure fluids are employed. Construction materials of increased tensile strength have encouraged the trend of high pressure utilization. From a practical point, the strength of any fluid pressure conduit or container is limited by the strength of the weld or connecting members which conbines the construction members to form the arrangement, pipe or the like. It is in this regard that numerous safety specifications and procedures have been published with a view to the testing of the pressure conduits, piping and the like. In such cases, the tests are usually conducted at pressures at least comparable to those at which the tubing will see service.

A common practice in the testing of fluid pressure conduit is to use the conduit to serve as a housing for a testing plug or device of the like. Generally, the testing plug is welded to the tube and may be cut off subsequent to the test performance. Remachining of the conduits is often required before the article can be shipped out.

SUMMARY OF THE INVENTION

The present invention basically comprises a modification of a standard type plug characterized by injection passages for introducing a fluid adhesive, air escape passages, centering means and pressure fitting means along with a method for using the same. Such an arrangement allows fluid pressure tight bonding to occur between the member being tested and the plug without the necessity of resorting to metal working operations for the attachment or detachment of the plug.

An adhesive material is injected through the fluid injection passages so as to settle in the border line area between the outer surface periphery of the plug and the inner surface of the tube or pipe into which the plug has been inserted. Centering means maintain the plug in position so as to be essentially coaxial with the conduit, while also serving as barriers to confine the fluid adhesive in the area desired. The adhesive is allowed to harden to form a pressure fluid tight seal. After the tube or pipe has been tested, the assembly is heated to soften the adhesive bond and the plug is then removed without the necessity of resorting to metal working operations or damaging the conduit so as to require remachining.

It is, therefore, a primary objective of the present invention to provide a hydrotest plug, the use and removal of which does not require remachining of the conduit.

It is another objective of the present invention to provide a hydrotest plug which is reusable.

An additional objective of the present invention is to provide a hydrotest plug which requires no welding for use in the test environment.

The various features of novelty which characterize the invention are pointed out with particularity in the claims annexed to and forming a part of this specification. For a better understanding of the invention, its operating advantages and specific objects obtained by its use, reference should be had to the accompanying drawings and descriptive matter in which there is illustrated and described a preferred embodiment of the invention.

DESCRIPTION OF THE PREFERRED EMBODIMENT

The present invention generally relates to testing equipment used in connection with ascertaining the pressure integrity of conduit type members and the like. More specifically, the present invention relates to a readily attachable and detachable hydrotest plug for testing the conduit's integrity which is used without requiring time consuming and costly welding rework of the members.

Figure 1:
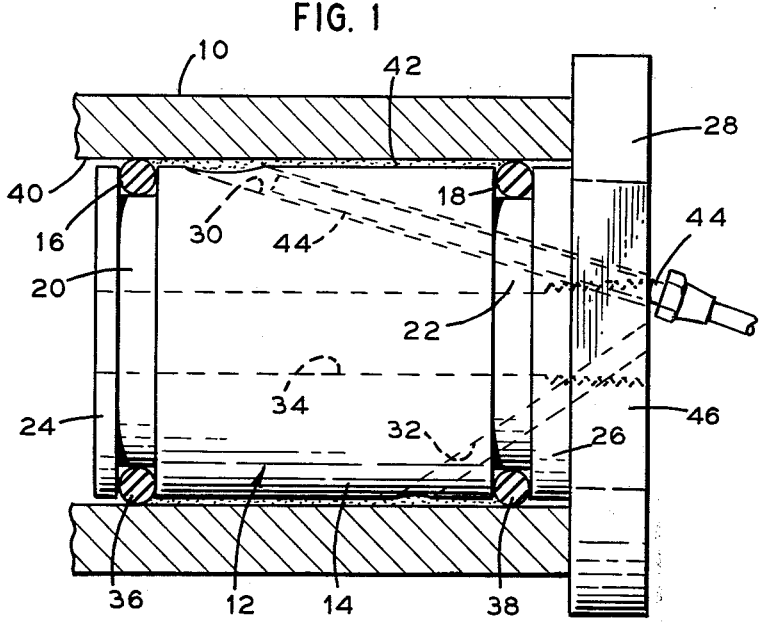
FIG. 1 is a cutaway view generally depicting the test plug with the fluid adhesive injection nozzle in place while the test plug is in place in a conduit like member for testing.

FIG. 1 generally depicts a conduit member 10 with the hydrotest plug 12 in position which may be designed for operating conditions ranging from essentially a full vacuum condition up to and including say 10,000 psig positive pressure. The abbreviation "psig" refers to the gauge pressure expressed in lbs. per square inch. Various codes and testing requirements must be met depending on the service condition which the vessel will experience.

FIG. 1 depicts the test plug 12 in use when inserted into the inside diameter of conduit member 10, hollow body, pipe or the like and is of dimension so as to snugly remain in contact with inner wall 40 of conduit member 10. The plug 12 comprises a body section 14 centrally located to the plug structure and forming one edge of each of the "O ring grooves" sections 16 and 18 with O ring bearing surfaces 20 and 22, respectively, Each of the O ring grooves 16 and 18 is completed by inner lip 24 and outer lip 26, respectively. Flush to outer lip 26 is flange 28. Body section 14, inner and outer lips 24 and 26, bearing surfaces 20 and 22 and flange 28 are all in coaxial relationship. The plug 12 is provided with both an internal passageway 30 for introduction of the fluid adhesive and an internal air or gas escape passageway 32, both of which are at an acute angle with respect to a common longitudinal axis of the test plug 12 and conduit 10. Passageways 30 and 32 cut the plug periphery at opposite ends of the plug body 14. As shown, the passageways meet the plug periphery not only at opposite ends of the plug body but also diagonally offset from one another. Also shown is passage 34 into which a pressure measuring device or drain valve (not shown) can be fitted. Front and rear O rings 36 and 38, respectively (only a portion of which are shown in FIG. 1) rest on bearing surfaces 20 and 22, respectively and cooperate with the outer surface of body section 14 and the inner surface 40 of conduit 10 to define an annular chamber 42 which is coaxial with body section 14. Adhesive passageway 30 and air escape passageway 32 provide access to chamber 42 when the plug 12 is in place in conduit 10. O rings 36 and 38 serve to provide a fluid tight seal to rigidly define the chamber 42 while also acting as centering means for the plug 12. FIG. 1 also shows how adhesive injection nozzle 44 appears when in operative position with plug 12. The injection nozzle is a simple tubular device which is connected to a source of fluid adhesive flowing under pressure. Such injection means is well known to those familiar with the art.

Figure 2:
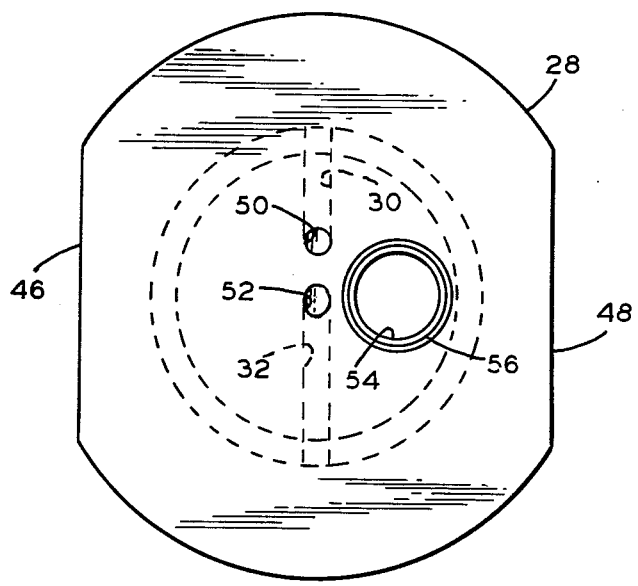
FIG. 2 shows an end view of the test plug but with the fluid adhesive injection nozzle removed.

FIG. 2, which is a view of plug 12 taken along the right hand side of FIG. 1, depicts the plug without the injection nozzle 44 present. As can be seen, flange 28 is not truly circular in geometry, but is provided with straight edges 46 and 48 which are in parallel relationship. Entrance 50 to passageway 30 and exit 52 from air escape passageway 32 are clearly shown and it will be noticed that they are centrally located with respect to the vertical axis of the flange 28. Opening 54 is preferably partially threaded 56 and is the entrance to passage 34 which extends the longitudinal distance of the device leading to the interior fluid environment of the conduit 10. As shown, such opening and passage may be slightly displaced from the vertical axis but preferably runs parallel to the longitudinal axis of the plug 12.

Figure 3:
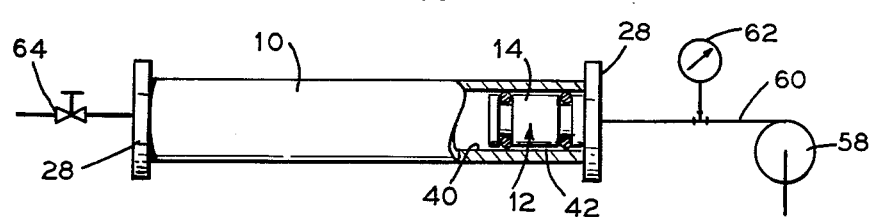
FIG. 3 shows an arrangement for using the test plug in testing a conduit like member.

FIG. 3 depicts the test plug 12 and apparatus arrangement for testing a conduit member 10. The invention may be used in the following manner. The inside and end edge of the conduit 10 are cleaned to remove foreign debris. The test plug is preheated to a temperature compatible with the adhesive to be used and, with the O rings 36 and 38 in place, is then inserted into conduit 10. The O rings, which are preferably composed of a fluorocarbon material, serve to center the plug in the conduit and to contain the fluid adhesive within a certain desirable area. The fluid adhesive is injected at approximately 25 psig into the chamber 41 area via fluid passageway 30. The chamber is formed by the periphery of the plug body 14, the O rings 36 and 38 and the inner wall 40 of the conduit 10. The pressurized fluid adhesive drives the air from the chamber area 42 which finds relief via air escape passageway 32. The entire plug is then rotated to uniformly spread the adhesive. Sufficient time is allowed for the particular adhesive to harden thus forming a strong flawless bond between the plug body 14 and the inner wall 40 of the conduit 10.

Subsequent to the bond formation, fluid is pumped via pump 58 through line 60 and passage 34 into the conduit 10. A pressure gauge 62 is located in the line so that the pressurized fluid imparts a reading to the gauge. The opposite end of the conduit member 10 may have a blind nipple flange or be equipped with a plug identical to plug 12. Drain valve 64 is opened to allow the air to escape and remains open until a strong stream of the fluid is the only effluent. Valve 64 is then shut and pump means 58 pressurizes the fluid to a pressure suitable according to the testing or code criteria. Following the test procedure, the fluid is allowed to drain by release of valve 64.

Subsequent to the testing procedures, the assembly is uniformly heated to approximately 500° F and removed by grippers applied to the linear edges of the plug flange 28. The plug is then further cooled by conventional means and after being cleaned by using an appropriate solvent, is ready for reuse.

In testing the above-described plug, which was originally designed for a 10,000 psi fluid pressure environment, it was found that certain advantages are had by preheating the plug prior to its placement in conduit member 10. Such temperature preconditioning made the adhesive flow easier and allowed the adhesive to cure more quickly thus reaching bond strength earlier. The adhesive used was of the two component epoxy based thermosetting variety as manufactured by United States Steel Company and sold under the NEXUS label. Curing temperatures and times were varied as well as the variety of the NEXUS compound employed. Evaluation was conducted mechanically using a 200,000 pound MTS tension-compression testing machine to measure the shear strength till failure. The results were then converted to equivalent hydrostatic pressures and showed that the minimum resisting pressure developed by the plug was 9,900 psi at a cure time consistent with that as recommended by the supplier of the adhesive.

The embodiment of the invention in which an exclusive property or privilege is claimed are defined as follows:

1. In a system using a test plug for testing the pressure integrity of that portion of a conduit member extending beyond the test plug, the conduit member being subjected to a fluid environment, the pressure characteristics of which vary from that of the environment surrounding the conduit member, the method of securing the test plug to the wall of the conduit member, the test plug having at least two internal passageways leading to the periphery of the test plug body, comprising:

placing and centering the test plug in the conduit member, injecting a fluid adhesive through one of the passageways into an annular chamber between the periphery of the test plug and a wall of the conduit member while allowing gas to escape the annular chamber through another of the passageways, allowing the fluid adhesive to harden to form a fluid pressure tight bond between the test plug and the wall of the conduit member, and subjecting the conduit member to the fluid pressure environment.

2. A method as in claim 1 wherein the fluid adhesive enters the annular chamber at one end of the plug body and the air escapes the annular chamber at the opposite end of the plug body.

* * * * *